(12) United States Patent
Densmore

(10) Patent No.: US 10,930,384 B2
(45) Date of Patent: Feb. 23, 2021

(54) METHODS FOR INTEGRATIVE DIAGNOSIS AND TREATMENT AND A KIT FOR THEIR IMPLEMENTATION

(71) Applicant: Martha Densmore, Brunswick, ME (US)

(72) Inventor: Martha Densmore, Brunswick, ME (US)

( * ) Notice: Subject to any disclaimer, the term of this patent is extended or adjusted under 35 U.S.C. 154(b) by 0 days.

(21) Appl. No.: 16/684,076

(22) Filed: Nov. 14, 2019

(65) Prior Publication Data

US 2020/0082929 A1    Mar. 12, 2020

Related U.S. Application Data

(63) Continuation of application No. PCT/US2018/040019, filed on Jun. 28, 2018.

(60) Provisional application No. 62/604,347, filed on Jul. 3, 2017.

(51) Int. Cl.
*G16H 20/90* (2018.01)
*A61H 39/08* (2006.01)
*A61K 9/00* (2006.01)

(52) U.S. Cl.
CPC .............. *G16H 20/90* (2018.01); *A61H 39/08* (2013.01); *A61K 9/007* (2013.01); *A61H 2201/102* (2013.01)

(58) Field of Classification Search
CPC .. A61H 39/08; A61H 2201/102; A61K 9/007; G16H 20/90
USPC .................. 434/106, 236; 705/2–3; 600/300
See application file for complete search history.

(56) References Cited

U.S. PATENT DOCUMENTS

| | | | |
|---|---|---|---|
| 2005/0008996 A1* | 1/2005 | Avivi-Meirson | A61B 5/167 434/236 |
| 2005/0112529 A1* | 5/2005 | D'Zmura | G09B 19/00 434/106 |
| 2007/0252812 A1* | 11/2007 | Keahey | G06Q 99/00 345/156 |

OTHER PUBLICATIONS

Gigi Hofer, Tarot Cards: An Investigation Of Their Benefit As A Tool For Self Reflection, Aug. 3, 2009, University Of Victoria, pp. 1-102 (Year: 2009).*

(Continued)

*Primary Examiner* — Joy Chng
(74) *Attorney, Agent, or Firm* — Caseiro Burke LLC; Chris A. Caseiro

(57) ABSTRACT

A kit and method for individual, family, or community psychological wellness diagnosis and a treatment for health enhancement are disclosed. The diagnosis is nursing compatible and based on Carl Jung's concepts of archetypes and synchronicity theory, and the treatment based on aromatherapy science and acupuncture theory. The kit includes a box with a plurality of containers and instructions for using the contents of the containers. Each container is labeled with one Jungian archetype and contains a unique aromatic substance. The method of the invention involves presenting the open box to the client or agent for assessment so that no more than a uniformity of top enclosures are visible, and timing their blind pick of one container. The picked archetype plus the timed number are both diagnostic; each supplies syntax for a psychological diagnosis of wellness health. A synchronicity time map supplies diagnosis words that bear like diagnostic meaning in three sciences: nursing, acupuncture, and Christian Science healing.

16 Claims, 3 Drawing Sheets

(56) References Cited

OTHER PUBLICATIONS

Sue Ellis-Saller, Essential Oils and Tarot Readings—The Basic Scents, Oct. 6, 2015, http://sueellissaller.com/2015/10/essential-oils-and-tarot-readings-the-basics/, pp. 1-14 (Year: 2015).*
International Search Report and Written Opinion in corresponding PCT application No. PCT/US2018/040019, dated Sep. 11, 2018, 8 pp.

* cited by examiner

METHODS FOR INTEGRATIVE DIAGNOSIS AND TREATMENT AND A KIT FOR THEIR IMPLEMENTATION

BACKGROUND OF THE INVENTION

Field of Invention

The invention relates to the field of Jungian psychology for psychological and spiritual analysis and to aromatherapy treatment. Specifically, the invention is a kit used by a healthcare provider to analyze an individual's psychological health in terms of an eminent archetype pattern plus a foundation of health word. The data supplies the correlates of an interdisciplinary integrated wellness diagnosis. The data is analyzed using the person's timed blind pick of one container from a series of essential oil containers labeled as tarot archetypes. A subsequent aromatherapy treatment uses the picked aroma in a topical application to archetype domain correlated, and time correlated, acupuncture points based on the diagnostic outcome of the analysis method.

Description of the Prior Art

The present invention was developed primarily in response to the human healthcare need for access to expanded definitions of psychological health and wellness, and a safe effective treatment that results when a method of making a clinical diagnosis uses a model of psychological health that includes a standardized nomenclature that is integrative, relevant, and usable across multiple fields in healthcare for psychological wellness assessment and aromatherapy treatment. The present method is based in Carl Jung's theory that synchronicity is a useful scientific method to gain psychological insights. It is based on Jungian psychology theory where archetypes in the collective unconscious includes the archetypes of the major arcana of the traditional tarot. It is based on aromatherapy science that shows that certain scents can improve brain function, enhance memory, mood, and psychological states. It is based on classical Chinese acupuncture theory where acu-points are portals for the human energy field where energy is accessed, transferred, balanced and harmonized including with essential oils. It is based on nursing science that sets forth an excellent model to format a description of wellness. It is based on Christian science mind healing where a word is held in thought to heal a person based on an understanding of the foundation of health.

A boundary object is an entity that facilitates communication between different social worlds including health disciplines. The present invention is directed to the human healthcare need for an integrative boundary object, both tangible and intellectual, that inhabits multiple healer disciplines and contributes a method to formulate an integrative diagnostic statement about a person's psychological wellness by analyzing a timed blind pick of a substance-archetype and then using the picked substance in a health treatment based on the diagnosis Patients and consumers across the globe use energy medicine for healing and to improve health. Many people in the United States receive healthcare to enhance and maintain already good health. Though a person may be faced with a life challenge or a psycho-spiritual burden, not all persons who receive psychotherapy are unwell. Vast populations of persons who receive psychotherapy in the healthcare industry are well and psychologically healthy. Many individuals receiving healthcare by a psychotherapist are not candidates for a medical or psychiatric diagnosis even though they are facing a life challenge or carrying burdens that are psychological, emotional or spiritual in nature. Jungian psychology, psychology and psychotherapy offer little to none standardized native nomenclature for a diagnosis of wellness health based on Jungian archetypes and synchronicity theory which are concepts recognized and applied in the field.

Psychologists and psychotherapists generally have no native taxonomy for a mental health wellness diagnosis outside of a psychiatric or medical diagnosis. The field of psychology has no native standardized diagnostic taxonomy to describe sickness or wellness. Many patients who are well, or who are getting well, engage in psychotherapy and receive psychotherapy care without the benefit of a wellness diagnosis. Professional registered nurses do diagnose wellness and have a native diagnosis taxonomy. The professional nurse uses nursing taxonomy to diagnose. But the field confines nursing diagnoses exclusively to the field of nursing. Nursing diagnoses are not well promoted and are underutilized by nurses including holistic nurses who practice aromatherapy.

Both the fields of nursing and acupuncture have a native taxonomy for making a health diagnosis. NANDA, the North American Nursing Knowledge Association, officiates and declares which words define the proprietary knowledge of nursing diagnoses. NANDA works to confine its nomenclature to nursing.

The claim is made by NANDA that "Nursing diagnoses define what we know—they are our words." However, several nursing diagnoses have in their structure common syntax that is present in diagnostic language of other health disciplines including the field of acupuncture. No one has yet organized a unity of cross-field diagnostic syntax in a diagnosis method that uses a kit invention. The kit advances the fields of Jungian psychology and holistic nursing by promoting the holistic clinician to actively diagnose wellness health and to treat clients based on the specific wellness diagnosis. The kit's method provides an additional diagnosis taxonomy to diagnose mental, emotional, and spiritual wellness.

Acupuncture is considered energy medicine because its anatomy and efficacy is not explainable using an evidence based biomedical model. However, acupuncture is gaining acceptance in the medical field. Christian Science healers are also energy medicine healers who work authentically outside of a biomedicine model. Evidence of Christian Science acceptability is that some insurance companies offered reimbursement for Christian Science treatments until the mid 1970s. Starting in the 1980s insurance companies began to reimburse patients for acupuncture treatments.

Holistic nurses practice aromatherapy both as a biomedicine and as energy medicine. Holistic nurses are an established field in nursing. Holistic nursing involves integrative healing modalities and processes that overlap with other fields. The holistic nurse may have multiple state licenses such as an acupuncture license, and may also be a psychotherapist who treats clients using aromatherapy and essential oils. Having a method to integrate a wellness diagnosis across multiple fields in healthcare benefits such professionals and their patients.

The common standard of using a medical diagnosis as the sole clinical description of health alienates groups of healers that have their own native taxonomy to describe health. A medical diagnosis is often a barrier when its meaning is fully alien to the authentic taxonomy of a health discipline. Through default, conditioned use, and allowances in scope of practice law, various disciplines that treat the same client often reluctantly use a medical diagnosis as the sole intellectual currency to describe health, even when the medical diagnosis is not aligned in any way with their native theory.

Medical diagnoses are generally sickness oriented disease and symptom labels. But clients also present with psychological wellness states that healers work to enhance, improve, and support by using aromatherapy and energy healing.

The present invention provides an appropriate assessment and treatment tool that integrates diagnostic data native to the separate science theories of Jungian psychology, nursing, classical acupuncture, and Christian Science healing. The link system is achieved through six word components that bear like diagnostic meaning in three health fields. It requires no adulteration of discipline identity to use the kit's taxonomy in describing health states. It's an additional taxonomy and treatment method for psychotherapists, holistic nurses, and other clinical practitioners.

The kit employs the theory of synchronicity. Synchronicity theory is used in Jungian psychology and many holistic methods. It is used in Christian Science healing in one method where a bible is opened to a random page to display text that is subsequently applied in thought for a healing. Christian Science was deployed extensively during WW1 and WW2 to heal the U.S. military including for physical and psychological problems. It is a demonstrated science.

The kit's random pick yields data of diagnostic synchronism that is based in Jungian psychology, primitive Daoist medicine, classical acupuncture science, and the Christian Science set forth by Mary Baker Eddy; a documented healing method since 1875. The ancient book *I Ching Book of Changes* employs a random toss of yarrow stalks or coins to yield synchronism that is diagnostic of life conditions including a client's mental health in a moment of time. The random blind pick is useful data containing an imprint of mental influences, beliefs, thought structure, emotion, spirituality, and circumstances in a moment of time.

The kit can be used to assess, analyze, and diagnose a person's mental, emotional, and spiritual wellness psychology based on synchronicity that exposes eminent and diagnostic archetypal patterns and foundations of health. Carl Jung, the founder of Jungian psychology, and other more recent scientists have documented that synchronicity is clinically significant though a method might appear to be random.

Archetypes are patterns in human experience that relate to health. In the United States Jungian psychologists treat clients and use concepts about archetypes including tarot archetypes as set forth by Carl Jung.

There are many types of tarot cards and medicine cards on the market to be used for healing. Some are purposed to informally diagnose states of mind and determine therapeutic directives. Cards are generally flat and are significantly different than a group of aromatic substances arranged as a kit of tarot substance-archetypes for the dual purpose of using a timed pick of a substance to formulate a multidiscipline inclusive integrative diagnosis, and then using the picked substance in a treatment indicated by the diagnosis.

Tarot cards have been around for hundreds of years. In tarot cards or medicine card type products it is common that a booklet is used to explain the card(s) that are picked or used. The present invention requires no theoretical speculation. All meanings are defined in simple syntax correlates and all taxonomy is standardized.

Acupressure, acupuncture, and aromatherapy use point locations on the body called acupuncture points or acu-points to modify and improve energy. Point locations and the method on how to locate points is commonly supplied in the form of a chart. The invention includes a chart of the location of the prescription acu-points.

Therapeutic essential oils are a popular treatment across many fields in healthcare. Aromatic substances including herbs and essential oils are topically applied by healers to acupuncture points. Aromatic substances are prescribed by acupuncturists, psychotherapists, holistic nurses, and healers for aromatherapy including to use as inhalants to improve health.

Applying aromatherapy to acupuncture points is not new. But the invention's method and process to formulate a psychological diagnosis based on a timed blind pick of a tarot archetype aroma and then applying the picked aroma to acupuncture points, based on the psychological domain of the picked archetype and also the timing, is new.

In a previous invention cards are used as a method for holistic diagnosis and Bach Flower treatment implementation. First, Bach Flowers treatment has no scent as it is homeopathy. Second, a selection from the cards is made based on an examination of color. In contrast, the present invention uses a "blind" random choice. Further, in any current market nowhere is any holistic diagnosis identified as part of a specific integrative diagnostic taxonomy of archetype based wellness states plus synchronistic time correlated wellness foundations. The stated example of Bach Flower cards has been used to assess psychological, personality, or thought process related states of mind. But the cards do not utilize syntax that is based on tarot archetypes, nor is it any protocol to formulate a wellness diagnosis in a format that is modeled in nursing diagnostic science.

Although many features of the present method and process are described in prior art, none of the prior art methods encompass a twenty-four aromatic substance-archetype schema of traditional tarot that uses a method of a timed blind pick of one archetype to generate a standardized diagnostic analysis that formulates a standardized diagnostic statement that is integrated because its foundation is based on integrated like diagnostic taxonomy in three health sciences. There is currently no professional healthcare kit designed as a method of psychological evaluation and diagnosis that uses aromatic substance-archetypes arranged as a tarot set based on Jungian psychology, tarot archetypes, synchronicity, and energy medicine including acupuncture, Christian Science, and holistic nursing aromatherapy.

SUMMARY OF THE INVENTION

The present invention is a kit of diagnostic vials for a person's psychological wellness analysis, diagnosis, and treatment. The vials are uniform in dimension and inside a box that closes on the top. The kit uses a method of a timed random pick of one vial to correlate a diagnosis and a treatment. Each vial is labeled on its side with one tarot archetype based on the traditional tarot card schema of 22 major arcana plus two more, the 2 lost archetypes. Each vial contains a single aromatic essential oil that is correlated to one tarot archetype to total 24 archetype aromas.

First, a brief summary of the method is described: The method of analysis to correlate an integrative diagnostic statement of psychological wellness starts with a person's timed random pick of 1 vial from a kit of 24 vials. The pick generates: 1 archetype, 1 aroma, 1 archetype theme, 1 archetype keyword, 1 archetype base diagnostic statement, 1 archetype domain, 1 domain generic diagnostic statement, 1 synchronistic number that is the recorded moment of the pick, and 1 synchronistic Component word correlated to the synchronistic number. The synchronistic number is a whole number of seconds between 0 to 60. Numbers are not rounded up and 0 is considered the same as 60. The time is recorded as the position of the second hand on a stopwatch when it is stopped at the moment of the pick. Regardless of how much time it takes for the pick the second hand is what is used to record a number of seconds between 0 to 60. This clocked number is the synchronistic time number and it is identified on a time map that correlates it to 1 Component word. The Component word is added to the archetype base statement to complete a standardized integrative diagnosis. Then, in a treatment process both the picked archetype domain and the Component contribute a prescription correlate of ordered acupuncture points. The acu-points are treated topically with the picked substance by applying the aroma using swabs held on the points for 30 seconds for each point. When one acu-point is located on both sides of the body they are treated at the same time.

When the kit is presented open only the vial tops are seen and they are uniform; the labels are not visible. A stopwatch is running before presenting the kit, before picking begins so that the time of the pick is always blind. Therefore, the method starts with a blind pick, "the pick" of one vial by a healthcare client. The healer uses a 60 second stopwatch to time where the second hand is at the moment the client picks one vial that is his selection. The stopwatch timing is conducted discreetly so as not to distract. The client may run fingers over the tops of the containers or not, think about an idea or not. It doesn't matter how long it takes. The healer stops the stopwatch when the client clearly picks and says "This one." As the healer or client retrieves the selected vial the tarot archetype is revealed. A chart lists each archetype's theme and keyword (Table 12). The healer then shares the following information with the client: the archetype's theme and keyword. Discussion of theory is not required.

The pick will be analyzed using an archetype chart and one of two time maps. The chart indicates the picked archetype's unique correlated base diagnostic statement (Table 4), a description that is diagnostic of the client's wellness health. The chart also indicates the archetype's correlated domain (Table 2). The domain of any archetype will be either mental, emotional, or spiritual (Table 2).

So the first part of the analysis yields a base diagnostic statement, one of 24, that describes the client's wellness health in terms of a domain: mental, emotional, or spiritual. The base statement will be part of the final diagnostic statement. It describes the client's wellness health as an eminent unfolding archetypal pattern with a locus of activation that is mental, emotional, or spiritual in nature. The archetype base statement describes a pattern that is finite and subject to change but that is diagnostic of the client's wellness health.

In the second part of the analysis, the integrative diagnostic statement is formulated by identifying the correlate of one of six Component words, the synchronistic Component, on a time map (Table 9, 10). The identified Component word is added to the beginning of the archetype diagnostic statement.

The Component taxonomy forms the acronym "WHISSH" and also "WISSH". The WHISSH taxonomy is a model of the foundation of health unique to the invention. Through analysis of the second of the pick, one Component is matched as the synchronistic Component. The synchronistic Component is also diagnostic of wellness health. It completes and integrates the final diagnostic statement.

The time map analysis identifies that one Component is the eminent, timely, and relevant foundation that is diagnostic of the client's sovereign wellness health through a relationship of synchronicity to the second of the pick. This matched word followed by a semi-colon is applied to the beginning of the archetype diagnostic statement to integrate it and to qualitate the new and final integrated diagnostic statement.

Three domain groups-consist of a set of 8 archetypes each (Table 2). So 8 archetypes are mental, 8 are emotional, and 8 are spiritual. The picked archetype's domain determines whether the base diagnostic statement is descriptive of a mental, emotional, or spiritual psychological pattern.

Unlike the archetypes which each inhabit only one of the client's three health domains, each Component word harmonizes and influences all three domains. The domain that is the primary locus in the integrative diagnosis is the domain of the picked archetype. Archetypes determine if the final diagnosis is mental, emotional, or spiritual in nature even though a Component has sovereign dominion over any archetype and its domain.

The final integrative diagnostic statement includes the base statement that is the primary presenting pattern clinically diagnostic of the wellness health. The final diagnostic statement also includes a Component of the client's eminent sovereign unchanging foundation of wellness health. All Components are part of the greater foundation of the client's health. But the pick timing identifies the one synchronistic Component that is eminent and diagnostically relevant in relation to the client and the identified archetypal pattern. Archetypes are finite and fallible, even if they are universal. The synchronistic Component has dominion over the presenting archetype and any of its activity or effects. The Component is a higher truth of the infinite omnipotent foundation of the client's actual health.

The Component is what integrates the diagnostic statement. The WHISSH Components are a taxonomy of diagnostic banner words. Each Component is a banner word comprised of hinged meaning matches; matches of diagnostic meaning sharing likeness across diverse fields including classical Chinese medicine (Table 6). Each Component is a unity word that bears like to like meaning in a stratum that crosses diagnostic taxonomy platforms in three sciences: nursing, acupuncture, and Christian Science healing (Table 6).

An integrative diagnostic statement in its complete form is referred to as a WHISSH I.D. or WISSH I.D. This does not preclude other diagnoses nor is it affected by them.

The six Components form the acronym WHISSH and are these words: Wholeness, Health, Intelligence, Science, Source, and Harmony (Table 5). An integrative diagnostic statement describes human health when it includes a WHISSH word Component, a banner bearing like meaning across the multiple fields. The Component qualitates the integrative diagnosis when its word is applied to an archetype diagnostic statement.

The process for the acu-point treatment involves applying the picked substance substrate to a series of acupuncture points, acu-points. The specific points to be used are dictated by the domain that the archetype belongs to and also the Component (Table 2, 3). So there are three acupuncture point groups, one for each domain. Plus, there is an additional acu-point in the treatment, the acu-point for the Component. The complete acu-point prescription is a description of a sequence of well-known acu-points and an order in which the acu-points are treated with the substance substrate. The healer mentally focuses on the words of the archetype's theme and keyword (Table 12) while applying the substrate to the acu-points indicated by the domain. The healer mentally focuses on the Component word (Table 5) while applying the substrate to the acu-point indicated by the Component (Table 3). The aroma is applied topically with a swab held on each point for 30 seconds each and where a point is located on both sides of the body they are treated together.

The analysis method and treatment process require no review with the client of theory, interpretations, meanings, or explanations in terms of the archetypes or aromatic substances. What is required is full attention to accurately record the pick time. Also required is that the healer learn the acu-point locations for the aromatherapy treatment. All instructions are given to the person being assessed prior to presenting the kit.

The method of using the kit is now described. Ahead of presenting the kit, a minute or more before the process of opening the kit the healer has started a stopwatch or clock mechanism to time the moment of a blind pick. The healer and person being assessed do not know where the second hand is on the running stopwatch. If the person is unable to pick a container, an appointed agent may do it. The picking is done in silence to avoid confusion. The person is instructed ahead of seeing the open kit to select one container and say "This one." The person is told to take his time; may pick quickly or slowly; run fingers over the tops of the containers while focusing on what he is feeling or thinking and so on. The pick can be for any reason and requires no reason. The 60 second stopwatch records the second number at the moment of a pick of one container. The healer stops the stopwatch on hearing "This one".

The healer stops the clock and notes the second hand number. The picked archetype and the clocked number are both analyzed. Even if the pick time has actually taken over a minute, the number is always 0-60 seconds. Numbers are not rounded up. 0 and 60 are considered the same number, both an even number.

Upon retrieval of the container the label is revealed showing the tarot identity of the substance-archetype to both the healer and the client. The healer discloses the archetype theme and keyword to the client. No discussion is required.

The picked archetype belongs to one of three domains: Man-Mental, Earth-Emotional or Heaven-Spiritual. The picked archetype generates one base diagnostic statement diagnostic of the patient's wellness health. This statement is not yet qualitated as integrative. The base statement describes the mental, emotional, or spiritual dynamic that is manifesting a synchronistic archetypal pattern and this dynamic is diagnostically relevant to a description of the person's wellness health. The pattern exists as a thought or belief system that is personal, communal, or more universal in nature.

The base statement is in a format generally consistent with a nursing diagnosis format. The base statement signifies the archetype pattern in a positive aspect. The acu-point aromatherapy treatment further promotes wellness and health. All of the wellness diagnoses, any combination of one archetype base statement plus one Component word, may apply to any person. But the person's timed pick is the dip stick in time measure of the person's wellness health that is a synchronistic pattern. Whatever is the recorded archetype pick and pick time, this is the current and correct data to be analyzed to correlate the complete integrative diagnosis of wellness.

Next, the number of seconds from the timed pick is analyzed by locating it on a time map. Finding the number on the time map will identify one Component word. This word, along with the archetype statement, is also diagnostic of the person's wellness health. The time number identifies the diagnostic synchronistic Component. The synchronistic Component is a word that completes, integrates, and qualitates a base archetype diagnostic statement to be a complete integrative diagnosis of wellness.

The synchronistic Component word integrates the diagnostic statement across three sciences because its word meaning includes subsets of like diagnostic word meanings that are matches across three sciences. The Component, when added to the base archetype statement, qualitates an integrative psychological diagnosis of wellness. Any of the 6 Components will qualitate any of the 24 base diagnostic statements as a WHISSH integrative diagnosis. The format for the complete integrated diagnosis statement is this: The Component word is followed by a semi-colon and placed at the beginning of the base diagnostic statement. This completes the format of the integrative diagnosis.

Each domain has one general overarching base diagnostic statement that applies to all of its eight archetypes (Table 2). This statement is a generic substitute for any of the domain's eight archetype base statements. If the client is averse or expresses opposition to the archetype or there is difficulty in using the archetype with the client, the generic diagnostic statement of the domain is substituted for the archetype base statement and used as the base statement. The acu-point prescription will be the same because the primary point prescription is determined by the domain. The Component's acu-point is based on the pick time and remains the same. The substrate used for the treatment remains the same. So the generic format does not change the acu-point prescription.

The archetype is categorized in one of three domains, more specifically: Heaven-Spiritual, Earth-Emotional, or Man-Mental. The domain (Table 2) supplies an over-arching significance of the pick including: a domain meaning, a domain jurisdiction, and a domain generic diagnostic statement which may be substituted for the archetype's base statement and used as a base statement in an integrative diagnosis. The domain supplies the primary prescription of acu-points. The Component contributes an additional acu-point to the prescription (Table 3). All of the acu-points are treated in a specific order (Table 2).

The timed second is the synchronistic number that is analyzed on one of two 60 second time maps: WHISSH or WISSH. The WHISSH map divides a minute into six 10-second bands of time (Table 9). The WISSH map divides a minute into five 12-second bands of time (Table 10). For odd numbers, the WISSH map is used with each band housing one Component each. For even numbers and 0, the WHISSH is map is used with each band housing one Component each. The healer locates the synchronistic number on the time map to correlate the one Component that is eminent and diagnostic of the person's foundation of health.

The WHISSH time map displays all 6 Components. In the 5 Component WISSH map, the Component of Health resides within the foundation of Harmony and the two are considered as one under the title and category of Harmony. So that in the WISSH map, when the pick time is an odd number, Health and Harmony are bonded together as one foundation and that is Harmony. So the five-word map does not include the word Health as a separate word because it is contained within the foundation of Harmony.

After the statement is completed, the kit's process involves treating designated acu-points in an integrative acu-aromatherapy healing treatment. The point prescription will be one of three groups of acu-points determined by the archetype domain plus one acu-point determined by the Component. The picked substance is applied to the points in the designated order (Table 2).

DETAILED DESCRIPTION OF THE INVENTION

Figure 1:
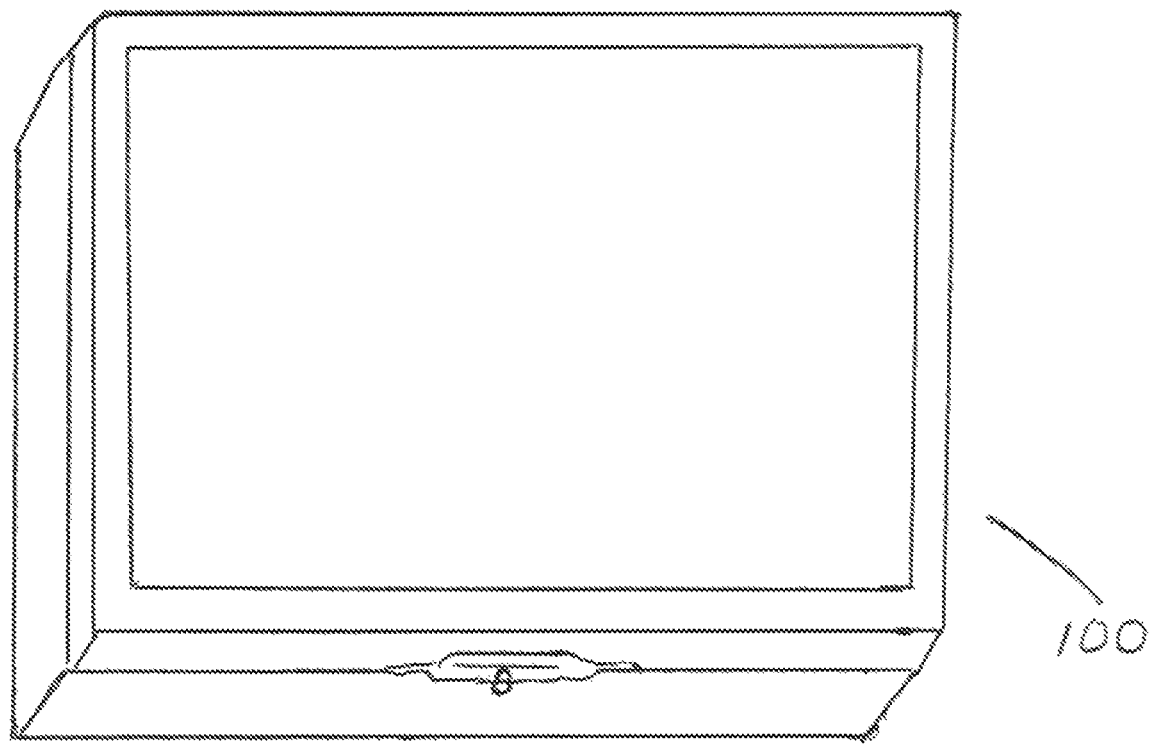
FIG. 1 is a plan view from above and shows the kit's box closed with a front clasp.
Figure 2:
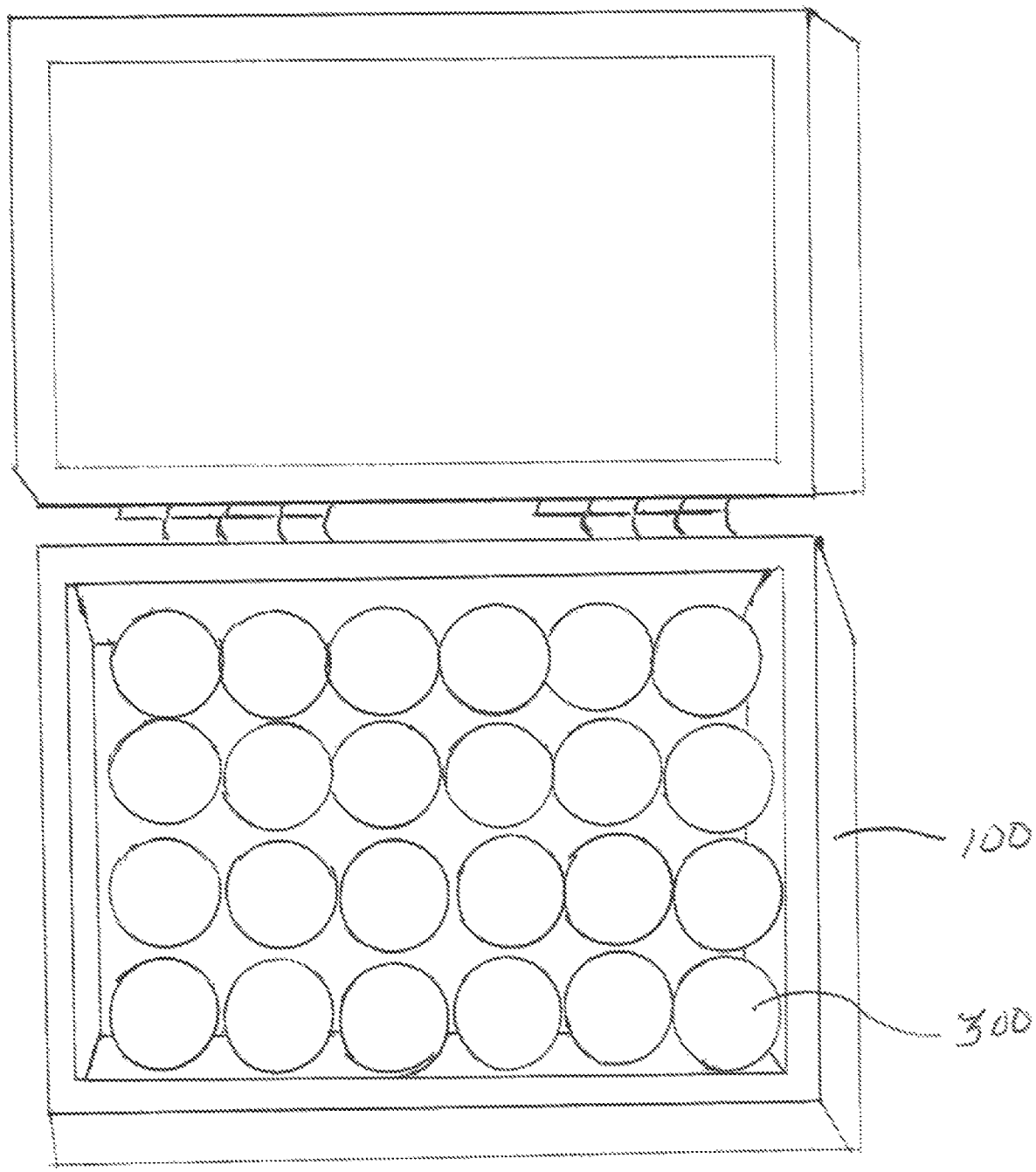
FIG. 2 shows a plan view from above of the kit with the box open and its container tops

In the present invention several preferred embodiments are described for illustrative purposes. Referring first to FIG. 1, a plan view showing the kit's closed box (100). FIG. 2 shows the present invention's open box with the total set of twenty-four vial containers. The view shown in FIG. 2 is the container top enclosures (300) which when the box is open are a uniformity that facilitates a random choice from which the client picks one vial, the pick.

Figure 3:
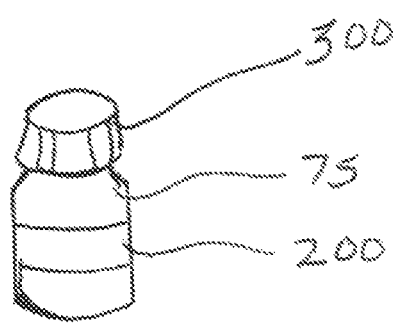
FIG. 3 shows the vial container, its closure top, and its data label.

The FIG. 3 shows one vial container (75) and its diagnostic side label (200) which identifies one of twenty-four major arcana tarot substance-archetype identities (Table 1). The FIG. 3 also shows the container cap enclosure (300) view from the side.

The total set is 24 unique tarot identities. The archetype sequence follows the twenty-two major arcana pattern of the well-established tradition set forth in the Rider-Waite tarot card deck. The invention varies from the 22 traditional major arcana labels in that two additional archetypes are added to total 24 major arcana (Table 1) according to the published theory of Onno and Rob Docters Leeuwen that sets forth that there are two additional tarot archetypes; the lost archetypes of Truth and Intuition. Per Leeuwen's theory, in the invention Truth and Intuition are not numbered but are identified with a symbol † or - next to the respective title as yang: † Truth; and yin: - Intuition.

The healer uses a stopwatch to record where the second hand is at the time of the pick. The watch is running before the kit is presented so that the timing is unpredictable. At the moment the client identifies his choice saying, "This one", the watch is stopped. The client is instructed to pick any vial he feels, thinks, or is intuitively drawn to. He may run his fingers over the tops during a short or long picking process. The pick reveals the label (200) of one of 24 tarot archetypes (Table 1). The archetype pick has a theme and a keyword (Table 12). The archetype pick has a base diagnostic statement (Table 4). The archetype will fit into one of three domains (Table 2). Table 2 also shows each domain has an over-arching meaning for its set of 8 archetypes; a jurisdiction that defines the sphere of activity of its archetypes, and one generic diagnostic statement that may be substituted for any of its 8 archetype's diagnostic statements.

The client's pick is an archetypal pattern that is synchronistic and diagnostic of his wellness health. The picked archetype will fall within a domain that is either a mental state, an emotional state, or a spiritual state (Table 2). The picked archetype is captured in a base diagnostic statement (Table 4) as an expression of a pattern of wellness which is understood to be in a finite continuum of development on a trajectory of progress. The pattern is diagnostic of a relationship, element or experience of the client that is presenting a condition of finite and fallible wellness. If there is a health challenge that the archetype is presenting such as a limitation or something unwanted, the base diagnosis is still worded as a positive wellness state (Table 4) and the acu-point treatment works to balance and harmonize any issues the client may be dealing with in relation to the pattern.

Each domain designates a specific prescription of acu-points (Table 2) with the order they are treated topically using the picked archetype substrate. Thus there are three groups of acu-points and whichever domain group the pick belongs to, that domain supplies the prescription for the specific protocol of points (Table 2) including the order of application (Table 2). An additional acu-point (Table 3) is added based on a time map analysis that generates a Component correlated acu-point.

Based on getting a timing as a count of seconds, 0-60, the healer analyzes a time map (Table 9, 10) to identify one of six foundation of health words, a Component (Table 5, 6, 7) that is the diagnostic synchronistic Component. Numbers are not rounded up. The number 0 and 60 are considered the same and an even number, the same slot on the clock. If the number of seconds is even, the healer uses the 6 Component WHISSH map (Table 9) for analysis. If the number is odd the healer uses the 5 Component WISSH time map (Table 10) for analysis. The healer matches the number from the stopwatch to the same number on the map. Whatever is the band of seconds for that number will contain the synchronistic Component that is diagnostic of the client's wellness health and that is used in the integrative diagnostic statement.

Each Component is a sovereign foundation that has dominion over all domains to dock, harness, and heal any imbalance related to an archetypal pattern. Any of the 6 Components may be used with any of the 24 base diagnostic statements. The time identified diagnostic Component is relevant in both the diagnostic statement and for the treatment. The healer adds the Component word to the base archetype diagnostic statement to complete the integration of the statement in three sciences; nursing, acupuncture, and Cristian Science healing. The final integrative statement describes the psychological wellness status of the client as an archetypal pattern docked in a foundation of health. The final statement begins with the time correlated Component word followed by a semicolon and then the correlated base archetype statement.

The time correlated synchronistic Component is the over-arching foundation of health that is always available to the client. This Component is a health agent working to preserve and promote the ever-present health that is the true wellness capacity of the client whether the client understands this or not. The Component foundation anchors the final and complete integrative diagnostic statement. The WHISSH I.D. describes a wellness state to be further supported, balanced, harmonized, and strengthened by applying the substance-archetype substrate to the correlated prescribed acu-points in an aromatherapy acu-point treatment.

The term "integrative diagnostic statement" in this invention means also to investigate, deduce, assess and evaluate a person for the purpose of treatment. The term "diagnostic statement" or "integrative diagnosis" is not meant to be limited to its ordinary meaning in the field of medical care, in which "diagnosis" may involve physical or psychological testing of a person. The diagnosis is not specifically related to or dependent on a medical diagnosis. The diagnostic statement is formulated using theory that is a unity of six words that each bear like meaning in three health science fields (Table 6). This unity is organized as the Components of Health, a complete model of the foundation of health.

The container side is labeled (200) with one archetype from a common traditional tarot taxonomy of major arcana archetypes (Table 1). Twenty-two of the labels are archetypes in a traditional sequential order plus two containers are labeled with a symbol † or - (Table 1). The labels are: Fool 0, The Magician I, The High Priestess II, The Empress III, The Emperor IV, The Hierophant V, The Lovers VI, The Chariot VII, Strength VIII, The Hermit IX, Wheel of Fortune X, Justice XI, The Hanged Man XII, Death XIII, Temperance XIV, The Devil XV, The Tower XVI, The Star XVII, The Moon XVIII, The Sun XIX, Judgement XX, The World XXI, Intuition - (counted as 23), Truth † (counted as 24).

The selected archetypes belong to one of three domains (Table 2). The domain is informed by Oriental medicine doctrine that explains that all mortal experiences reflect interplay and equilibrium of Heaven and Earth, and that Man mediates between Heaven and Earth. The Heaven, Earth, and Man domains filter meanings and spheres of activity of the archetypes wherein they are organized as 3 groups of 8 tarot substance-archetypes (Table 2). Oriental medicine theory further contains the idea that Heaven relates to spirituality, Earth relates to emotions or animal instincts, and Man relates to mental thought capacity to reason and mediate between Heaven above and Earth below. Each domain has a protocol of acu-points including the order that they are treated topically with the substance-archetype (Table 2). A description of the location of the acu-points is included with the kit (Table 11).

The three domains of Heaven-spiritual, Earth-emotional, and Man-mental are based on ancient Oriental medicine and Christian Science theory as set forth by Mary Baker Eddy. Each domain is a jurisdiction that defines the sphere of activity of its archetypes (Table 2). The three domains are idealized states of mortal existence.

The domains exist as states of wellness health. They highlight progress and development of archetypes along this path. The domains are structured as follows: Heaven-Spiritual is ideal spiritual mind ruled by divine principle. Earth-Emotional is the sphere the physical sensory processes and emotions that are finite and limited. The domain of Man-Mental is where thought, reason, and experience work to mediate between Heaven and Earth. This includes critical thinking, reasoning, and the mental activity that resolves problems and destroys error. Man develops through spiritual sense and morality to rise above poor thought models, conditioning, hypnosis, and habit.

The archetypes are finite fallible patterns of activity in a continuum of unfolding health and development of a domain. For the holistic nurse the kit's archetypes are patterns, challenges, and or needs related to the client's actual or potential life processes related to health, wellness, human responses, and or illness.

The archetype pattern may involve things that are positive or negative including setbacks. The pick presents archetypal activity in a domain and the treatment works to purify and harmonize this archetype and any of its manifestations in the client's life experience so that good health is promoted and supported.

Each Component is a single word. The meaning of the Component word is understood as but not limited to its literal meaning in English. The 6 Components are banner words comprising definitions of like diagnostic meanings (Table 6) in three health sciences: classical Daoist Chinese acupuncture, nursing, and the Christian Science healing method set forth by Mary Baker Eddy in her textbook *Science and Health with Key to the Scriptures*. The Component words are: Wholeness, Health, Intelligence, Science, Source, Harmony (Table 3, 5, 6, 7). Their definition includes as a continuum (Table 7) of a foundation to support archetypes and archetype domains.

The Component is used to complete and qualitate an archetype's base diagnostic statement into the form of an integrative diagnostic statement referred to as a WHISSH I.D. The WHISSH I.D. is a sharable taxonomy used by Jungian psychologists, holistic nurses and multi-discipline integrative teams involved with holistic healing.

The 6 Components align and integrate health data across a unified field of meaning within the three sciences. A variety of disciplines may uniformly organize the diagnostic data to analyze a professional diagnostic statement and perform an acu-point protocol aromatherapy treatment.

The 6 Components are understood to be perfect states as the macrocosm and also as a continuum of perfect unfoldment on a path of progress as microcosm. (Table 7).

The kit offers the additional advanced option that the client may contemplate a Q Word during the picking process (Table 8). The Q word is identified prior to opening the box. It requires an additional clocked time of 0-60, a number of seconds on a stopwatch and 0 is the same as 60. The client is instructed to relax, feel at peace, take some moments and simply indicate "now" for the watch to be stopped in a moment of time. The timing process is the same as for the pick with the watch running prior to start. The clocked time is correlated on the Q Map chart to a word and meaning to contemplate during the pick process. The client is simply told the word and its meaning (Table 8).

After the pick and before the treatment the healer will share or confirm with the client the name of the picked archetype, its theme and keyword (Table 12).

After the WHISSH I.D. is formulated the patient is treated for the diagnosis. The healer does this by applying the substrate to the indicated acu-points in an acu-aromatherapy treatment to harmonize, balance, and support good health. The healer applies the substrate to specific acu-points based on the diagnosis. The treatment protocol for the acu-points is dictated by the archetype's domain that has a set and order of acu-points (Table 2). The additional acu-point for the Component (Table 3) will be positioned in the order of application based in the domain prescription (Table 2).

The invention includes a chart that describes the location of the commonly used acu-points. The acu-points are named and their location on the body is described in common nomenclature (Table 11). These points are commonly used by massage therapists and energy healers and a person of ordinary skill in the art can learn their location for the acu-aromatherapy treatment. So the substance is applied topically to acu-points on the skin, all in a specific order-based on the domain of the picked archetype (Table 2).

The substrate is applied to acu-points with a short swab that is saturated with the substrate. The healer makes contact with the acu-point and holds the contact position for 30 seconds. For an acu-point that is located on both sides of the body, both acu-points are treated together with one swab in each hand. The healer works through the prescription of points in the indicated order. The healer mentally focuses on the picked archetype's theme first and then on the keyword (Table 12) while treating each of the domain acu-points. The healer mentally focuses on the Component word while treating the acu-point that correlates with the Component (Table 5, 3).

For treatment purposes, the Component is an expression of the client's infinite foundation of health. The Component is an application of truth during the acu-aromatherapy treatment. It balances the archetype in all three domains, mentally, emotionally, and spiritually. It balances the archetype in relationship to the client during the acu-point treatment, and the Component acu-points are where this energy is accessed and harmonized on the body.

Although only a preferred embodiment is specifically illustrated and described herein, it will be appreciated that many modifications and variations of the present invention are possible in light of the above teachings and data organization wherein the purview of the appended claims without departing from the spirit and intended scope of the invention.

TABLE 1

| TAROT KIT ARCHETYPE | ARCHETYPE AROMATIC SUBSTANCE |
|---|---|
| Fool 0 | Nutmeg |
| The Magician I | Fennel |
| The High Priestess II | Ylang Ylang |
| The Empress III | Sandalwood |
| The Emperor IV | Juniper |
| The Hierophant V | Bergamot |
| The Lovers VI | Cinnamon |
| The Chariot VII | Jasmine |
| Strength VIII | Angelica |

TABLE 1-continued

| TAROT KIT ARCHETYPE | ARCHETYPE AROMATIC SUBSTANCE |
|---|---|
| The Hermit IX | Lavender |
| Wheel of Fortune X | Sage |
| Justice XI | Lemon Balm |
| The Hanged Man XII | Vanilla |
| Death XIII | Basil |
| Temperance XIV | Vetiver |
| The Devil XV | Cypress |
| The Tower XVI | Pine |
| The Star XVII | Anise |
| The Moon XVIII | Neroli |
| The Sun XIX | Frankincense |
| Judgement XX | Eucalyptus |
| The World XXI | Wintergreen |
| Intuition- | Clary Sage |
| Truth † | Chamomile |

TABLE 2

| Domain: | Heaven-Spiritual | Earth-Emotional | Man-Mental |
|---|---|---|---|
| Meaning: | Divine Spirit, God, Dao, Eternal, Unlimited, Divine Mind All Knowing, Ever Present, Infinite Power, Soul, Spiritual Sense, Even Rule, Government by Divine Principle, Spirituality, Bliss. | Anger Joy Worry Grief Fear | Unfolds spiritually on a path between Heaven and Earth; Finite mortal ideas of sin, sickness and death dissolve in reasoned and progressive footsteps of spiritual experience and understanding. |
| Jurisdiction: | Spiritual | Emotions, Beliefs, Instincts | Intellect, Reason, Morality, Virtue |
| Generic overarching diagnostic statement the domain | Readiness for enhanced spirituality | Readiness for enhanced emotional wellness and resilience | Readiness for enhanced cognitive mental health |
| Archetypes: | TRUTH MAGICIAN EMPEROR CHARIOT WHEEL of FORTUNE DEATH TOWER SUN | FOOL EMPRESS LOVERS HERMIT HANGED MAN DEVIL MOON WORLD | INTUITION HIGH PRIESTESS HIEROPHANT STRENGTH JUSTICE TEMPERANCE STAR JUDGEMENT |
| Acupuncture points in order that they are treated: | 1. Ear: Shen Men 2. Ear: Heart 3. L.I. 4 4. Liv. 3 5. Spleen 6 6. Component Point | 1. L.I. 4 2. Liv. 3 3. Lung 9 4. PC 6 5. Spleen 3 6. Kid. 2 7. Component Point | 1. Ear: Shen Men 2. Ear: Liver 3. L.I. 4 4. Liv. 3 5. G.B. 20 6. Anmian 7. Component Point |

TABLE 3

| Wholeness Acu-point | Health Acu-point | Intelligence Acu-point | Science Acu-point | Source Acu-point | Harmony Acu-point |
|---|---|---|---|---|---|
| L.I. 11 | Yin tang | Ren 17 | Du 20 | St. 36 | Lung 7 |

TABLE 4

| ARCHETYPE | Base Diagnostic Statement |
|---|---|
| Fool 0 | Prepared upon a greater care with resilience to unhealthy risks, harm, or damage. |
| The Magician I | Prepared upon a greater catalyst with cause to manifest, manage, and maintain a good outcome. |
| The High Priestess II | Prepared upon a greater vantage with historical perspective, wisdom, knowledge, and values. |

TABLE 4-continued

| ARCHETYPE | Base Diagnostic Statement |
|---|---|
| The Empress III | Prepared upon a greater nature with lush creative flow, comfort, and support to bear good fruit. |
| The Emperor IV | Prepared upon a greater dominion with a foundation for correct organization, order, and morality. |
| The Hierophant V | Prepared upon a greater doctrine anchored in correct data that achieves advancement. |
| The Lovers VI | Prepared upon a greater alignment with discretion to value integrity, authenticity, and enhanced relationship. |
| The Chariot VII | Prepared upon a greater vehicle with protection, safety, and guidance for the journey. |
| Strength VIII | Prepared upon a greater capacity with inner knowing that anchors self-care, passion, and love. |
| The Hermit IX | Prepared upon a greater reserve with reverence for solitude, sacred retreat, and intimate relationship. |
| Wheel of Fortune X | Prepared upon a greater field with the freedom to choose and a choice that is right. |
| Justice XI | Prepared upon a greater court with accountability to build esteem of self and others in a trustworthy record. |
| The Hanged Man XII | Prepared upon a greater perspective to cope efficiently. |
| Death XIII | Prepared upon a greater model with living that transcends fear, death, anxiety, suffering, and mortal illusion. |
| Temperance XIV | Prepared upon a greater rule with an accurate measure for personal identity, influences, and circumstances. |
| The Devil XV (a.k.a. Trickster) | Prepared upon a greater power with absolute authority for high governance, self-love, and trauma release. |
| The Tower XVI | Prepared upon a greater platform with the solid sense of grounded support, safety, and serenity through change. |
| The Star XVII | Prepared upon a greater alter with the measure that heals body-image, human dignity, all sentient experience. |
| The Moon XVIII | Prepared upon a greater continuity with care and rest in the presence of conflict, discomfort, pain, and doubt. |
| The Sun XIX | Prepared upon a greater love with the hope that can shoot with heart and shine with confidence. |
| Judgement XX | Prepared upon a greater scale with the mind to make a good decision and the means to keep a contract. |
| The World XXI | Prepared upon a greater destiny with the mastery that succeeds in completion. |
| Intuition- | Prepared upon a greater channel with reception to capture angelic insights, inspiration, and spiritual understanding. |
| Truth † | Prepared upon a greater truth with the good facts that answer those questions that measure up. |

TABLE 5

| Component | General Meaning |
|---|---|
| Wholeness | Wholeness, Integration, Unity, Fullness, All |
| Health | Spiritual-Moral-Mental-Intellectual Soundness, Well-being |
| Intelligence | Understanding, Wisdom, Problem-solving, Discovery, Reasoning, Knowledge, Logic, Education, Morality, Awareness, Teach-ability, Watch, Conscience, Capability |
| Science | Scientific method, Process, Way, Discipline, Teaching, Technology |
| Source | Divine Mind, Sacred Source, Essence, Life, Energy, The Universe, Higher Power |
| Harmony | Health and Wellness, Morality, Truth, Love, Enhancement, Continuity, Rightness, Even, Complement, Balance, Coherence, Agreement, Accord |

TABLE 6

| Component Name as Banner Meaning Hinge System | Holistic Nursing Meaning Hinge | Acupuncture Meaning Hinge | Christian Science Meaning Hinge |
|---|---|---|---|
| Wholeness | Relationship-centered, Interconnectedness of self, others, nature, and spirituality | Complete pattern of interconnected cooperating parts of Macrocosm as in the Microcosm and its parts each whole | Infinite, All, Blessed relationship, Spiritual law, Unity of good |
| Health | Integration into Wholeness, Harmony, Unity, Balance | Harmony and Balance | Absolute consciousness of Harmony |
| Intelligence | Wisdom | Xin, Soul, Heart | Spiritual understanding |
| Science | Holistic Health Cultivation | Superior Man Cultivation | Divine Man Cultivation |
| Source | Spirituality, individual sense of deeper connectedness with transpersonal Sacred Source | Dao | Divine Mind, God |
| Harmony | Support for health in all human experience | Mutually supportive relationship of Yin and Yang | Radiant reflection of good |

TABLE 7

| Component | Continuum of Component |
|---|---|
| WHOLENESS | Continuum of integration, completion, unity |
| HEALTH | Continuum of harmony, balance |
| INTELLIGENCE | Continuum of knowledge, ability, understanding, wisdom |
| SCIENCE | Continuum of revelation, technology, process |
| SOURCE | Continuum of life, love, energy, blessing, will |
| HARMONY | Continuum of consonance, agreement, accord |

TABLE 8

| Q Words | Q Word Meaning | Match for Clocked Second |
|---|---|---|
| ANGER | Anger to Serenity | 1, 11, 21, 31, 14, 51 |
| JOY | Joy to Serenity | 2, 12, 22, 32, 42, 52 |
| RUMINATION | Rumination to Serenity | 3, 13, 23, 33, 43, 53 |
| GRIEF | Grief to Serenity | 4, 14, 24, 34, 44, 54 |
| FEAR | Fear to Serenity | 5, 15, 25, 35, 45, 55 |
| RESENTMENT | Resentment to Serenity | 6, 16, 26, 36, 46, 56 |
| SELF-PITY | Self-pity to Serenity | 7, 17, 27, 37, 47, 57 |
| GLUTTONY | Gluttony to Serenity | 8, 18, 28, 38, 48, 58 |
| ENVY | Envy to Serenity | 9, 19, 29, 39, 49, 59 |
| DISHONESTY | Dishonesty to Serenity | 10, 20, 30, 40, 50, 60, 0 |

TABLE 9

| Time Map WHISSH for Even #s | Time Range Communicant in Seconds | Seconds |
|---|---|---|
| Wholeness | 0-8 and 60 | 0, 2, 4, 6, 8, 60 |
| Health | 10-18 | 10, 12, 14, 16, 18 |
| Intelligence | 20-28 | 20, 22, 24, 26, 28 |
| Science | 30-38 | 30, 32, 34, 36, 38 |
| Source | 40-48 | 40, 42, 44, 46, 48 |
| Harmony | 50-58 | 50, 52, 54, 56, 58 |

TABLE 10

| Time Map WISSH for Odd #s | Time Range Communicant in Seconds | Seconds |
|---|---|---|
| Wholeness | 1-11 | 1, 3, 5, 7, 9, 11 |
| Intelligence | 13-23 | 13, 15, 17, 19, 21, 23 |
| Science | 25-35 | 25, 27, 29, 31, 33, 35 |
| Source | 37-47 | 37, 39, 41, 43, 45, 47 |
| Harmony | 49-59 | 49, 51, 53, 55, 57, 59 |

TABLE 11

| Acu-point | Location |
|---|---|
| Ear: Shen Men | Located slightly superior and central to the curving tip of the Triangular Fossa of the ear |
| Ear: C1 Heart | Located at the deepest most central area of the inferior concha of the ear |
| Ear: Liver | Found on the peripheral Concha Ridge and Concha Wall of the ear |
| Large Intestine 4 | On the dorsum of hand, between $1^{st}$ and $2^{nd}$ metacarpal bones, in the Middle of the $2^{nd}$ metacarpal bone on the radial side |
| Liver 3 | On the dorsum of the foot in the depression distal to the junction of the first and second metatarsal bones |
| Spleen 6 | Located the breadth of 3 fingers directly above the medial malleolus on the posterior border of the medial aspect of the tibia bone |
| Lung 9 | Located on the radial end of the transverse crease of the wrist in the depression on the lateral side of the radial artery |
| Pericardium 6 | Located the breadth of 2 fingers above the transverse crease of the wrist between the tendons of the medial palmaris longus and the medial flexor radialis |
| Spleen 3 | Located proximal and inferior to the head of the first metatarsal bone at the junction of the red and white skin, or meeting of skin colors |
| Gall Bladder 20 | Located in the depression of the upper portion of the SCM muscle and the trapezius muscle on the same level with Du 16 that is just below the occipital protuberance |
| Anmian | Behind the ear midway between Gall Bladder 20 and San Jiao 17 |
| Kidney 2 | Anterior and inferior to the medial malleolus the point is in the depression on the lower border of the tuberosity of the navicular bone |
| Large Intestine 11 | When the elbow is flexed the point is at the depression at the lateral end of the transverse cubital crease, midway between Lung 5 and the lateral epicondyle of the humerus bone |
| Yin Tang | Located midway between the medial ends of the eyebrows |
| Ren 17 | Located on the anterior midline at the level of the $4^{th}$ intercostal space |
| Du 20 | Located on the midline of the head, on the midpoint of the line between the apexes of the two auricles |
| Stomach 36 | Located below the knee the breadth of 3 fingers below Stomach 35, 1 finger breadth lateral to the anterior crest of the tibia |
| Lung 7 | Above the wrist, superior to the styloid process of the radius, 1½ finger breadth above the transverse crease of the wrist |

TABLE 12

| TAROT ARCHETYPE | THEME | KEYWORD |
| --- | --- | --- |
| Fool 0 | Thoughtful | Resilience |
| The Magician I | Catalyst | Substantive |
| The High Priestess II | Relative | Memory |
| The Empress III | Creative | Flow |
| The Emperor IV | Govern | Reverence |
| The Hierophant V | Craft | Precision |
| The Lovers VI | Align | Discernment |
| The Chariot VII | Vehicle | Protection |
| Strength VIII | Capacity | Power |
| The Hermit IX | Sacred | Inspiration |
| Wheel of Fortune X | Prosperity | Wealth |
| Justice XI | Imprint | Good |
| The Hanged Man XII | Suspension | Spiritual |
| Death XIII | Transcendence | Energy |
| Temperance XIV | Equilibrium | Support |
| The Devil XV | Error | Correction |
| The Tower XVI | Change | Stability |
| The Star XVII | Healing | Love |
| The Moon XVIII | Continuous | Serenity |
| The Sun XIX | Brilliance | Confidence |
| Judgement XX | Decision | Guidance |
| The World XXI | Mastery | Success |
| Intuition- | Message | Reception |
| Truth † | Mind | Expression |

The invention has been described with respect to specific examples. It is not intended to be limited to those examples. The scope of the invention is defined by the following claims and equivalents.

What is claimed is:

1. A method for individual psychological diagnosis using a kit including a box, an archetype chart, two time maps, and instructions, wherein the box is used to removably retain therein a plurality of aromatic substances contained in a corresponding number of closed containers that are each labeled on a side thereof with a different tarot archetype, and wherein the instructions enable a healer to carry out a psychological diagnosis of a person to establish a base diagnostic statement and an integrative diagnostic statement for the person, the method comprising the steps of:
   starting a stopwatch or clock by a healer;
   instructing a person by the healer to select by random blind pick one of the closed containers located in the box;
   stopping the stopwatch or the clock by the healer upon the healer observing the selection by the person of the one container located in the box;
   noting by the healer of the seconds only registered on the stopwatch or clock upon stopping the stopwatch or the clock, wherein the noted seconds is a number between 0 and 60 that is a picked time number;
   observing by the healer of the tarot archetype labeled on the side of the selected container and generating a base diagnostic statement of the person's wellness health using the archetype chart; and
   observing by the healer the picked time number noted on the stopped stopwatch or clock and identifying it as a clocked number;
   matching by the healer of the clocked number with a time matched correlated word using one or both of the two time maps; and
   generating by the healer an integrative diagnosis statement of the person's wellness health using the time matched correlated word from the one or both of the two time maps.

2. The method of claim 1, wherein the time matched correlated word has a definition that bears like to like meaning to similar words and phrase clusters used in diagnostic statements across the plurality of nursing, acupuncture, and Christian Science healing.

3. The method of claim 1, wherein the time matched correlated word bears like to like meaning integrated through three sciences so that the time correlated word is one of the following group of 6 words: Wholeness, Health, Intelligence, Source, Science, Harmony.

4. The method of claim 3, wherein each of the six words is diagnostic of a person's greater foundation of wellness health that is not transitory, finite, or episodic.

5. The method of claim 4, wherein one word is diagnostic of a person's foundation health so that the word is applied by the healer to an archetype diagnostic statement that includes a standardized archetype diagnostic statement and a standardized integrative word diagnostic of a health foundation.

6. The method of claim 5, wherein if the clocked time is an odd number then the correlate diagnostic word will be found by the healer on one of the two time maps that has one minute divided into 5 bands of consecutive seconds, and if the clocked time is an even number the correlate diagnostic word will be found by the healer on one of the two time maps that divides one minute into 6 bands of consecutive seconds.

7. The method of claim 1, wherein the healer ensures that the clocked number is always a whole number from 0 to 60 and that any timed number with a fraction is not rounded up but is rounded down to a whole number from 0 to 60.

8. The method of claim 1, wherein the timing of the person's pick includes use of a clock mechanism in such a way as to have the stopwatch or clock running before the picking process to ensure a blind pick as to the time which is always recorded as a number of seconds from 0 to 60 in one minute, and 0 is treated the same as 60, regardless of how many minutes have passed so that the time is always a number of 0-60 seconds.

9. The method of claim 1, wherein the step of generating the integrative diagnostic statement includes the step of the healer using a time mapped organization of one or both of the two time maps of six words diagnostic of health where each word corresponds to a unit band of seconds of time so that each second corresponds to one of 5 or one of 6 bands based on if the second is odd or even when the aromatic substance picking occurs.

10. The method of claim 1, wherein the step of generating the integrative diagnostic statement includes identifying by the healer one diagnostic word through finding its placement in a band of seconds that houses the second that is the number of a person's timed pick.

11. The method of claim 1, wherein the pick time number is a second that correlates to one of six diagnostic words and the word is diagnostic because its time value is the same value as the time of the pick, measured as a number of seconds that is a match.

12. The method of claim 1, wherein the tarot archetype on the picked container indicates a prescription of specific acupuncture points in an order where each acu-point is treated in the order by the healer applying the picked substance topically to the prescribed acu-point located on the body and ear of the person as described in an acu-point location chart to support and improve psychological, mental, emotional, and spiritual health of the person making the pick.

13. The method of claim 12, wherein the treatment regime is based on classical acupuncture point function, and aromatherapy science of scent.

14. The method of claim 12, wherein the timed blind pick correlates to one of six synchronistic diagnostic words, wherein each of the six words correlates to a prescription of one acupuncture point.

15. The method of claim 14, the six synchronistic diagnostic words are selected by the healer from the group comprising: Large Intestine 11; YinTang; Ren 17; Du 20;
Stomach 36;
Lung 7.

16. The method of claim 15, wherein the match of a time correlated diagnostic word by the healer to a correlated acupuncture point comprises the following six matches: Wholeness is Large Intestine 11; Health is YinTang; Intelligence is Ren 17; Science is Du 20; Source is Stomach 36; Harmony is Lung 7.

* * * * *